United States Patent
Snyder

Patent Number: 4,569,797
Date of Patent: Feb. 11, 1986

[54] PRODUCTION OF ISOXANTHATE SALTS AND DITHIOCARBONATE DIESTERS

[75] Inventor: Donald M. Snyder, Hampton, Va.

[73] Assignee: Virginia Chemicals Inc., Portsmouth, Va.

[21] Appl. No.: 522,219

[22] Filed: Aug. 11, 1983

[51] Int. Cl.⁴ ............................................. C07C 154/02
[52] U.S. Cl. ................................................ 260/455 B
[58] Field of Search ..................................... 260/455 B

[56] References Cited

U.S. PATENT DOCUMENTS 2,161,566  6/1939  Fuller ............................ 260/455 B
2,436,051  2/1948  Mixon ..................................... 267/7

OTHER PUBLICATIONS

Hackh's Chemical Dictionary, McGraw-Hill Book Company, New York, (1969) p. 371.
Noller, Textbook of Organic Chemistry, W. B. Saunders Co., Philadelphia, 1966, p. 63.

*Primary Examiner*—Henry R. Jiles
*Assistant Examiner*—Robert C. Whittenbaugh
*Attorney, Agent, or Firm*—Depaoli & O'Brien

[57] ABSTRACT

This invention provides a process for preparing a novel class of isoxanthate salts, such as sodium S-benzylisoxanthate:

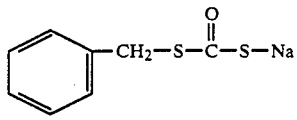

The process involves a reaction between carbonyl sulfide and a metal mercaptide under aprotic conditions.

This invention further provides a process for converting a metal mercaptide via an isoxanthate salt intermediate to a dithiocarbonate diester such as dimethyl dithiocarbonate:

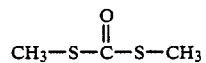

These compounds have found application as rust inhibitors, plasticizers, insecticides, herbicides and the like.

15 Claims, No Drawings

PRODUCTION OF ISOXANTHATE SALTS AND DITHIOCARBONATE DIESTERS

BACKGROUND OF THE INVENTION

Dithiocarbonate diesters are organic compounds which exhibit a broad range of valuable properties. Various species have found application as rust inhibitors in oil formulations, rubber plasticizers, cytostatic antitumor agents, antituberculosis agents, ovicides, insecticides, herbicides, fungicides, plant growth regulators, photographic silver halide emulsion stabilizers, and the like.

U.S. Pat. No. 2,476,166 describes $\alpha,\alpha'$-dithiocarbonodialiphatic acids which are useful as rust inhibitors in turbine oils.

U.S. Pat. No. 2,775,568 describes the plasticizing of rubbers with dithiocarbonate esters such as dipentachlorophenyl dithiocarbonate.

U.S. Pat. No. 3,151,024 describes new biological toxicants with a dithiocarbonate diester structure:

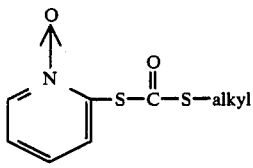

U.S. Pat. No. 3,510,486 describes the preparation of ovicidal agents such as 6-methylquinoxaline-2,3-dithiol cyclic carbonate:

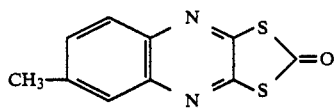

The most common synthesis method for the production of dithiocarbonate diesters involves the reaction of phosgene and an appropriately selected mercaptan:

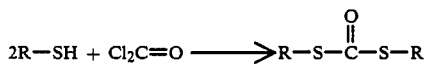

In order to prepare an unsymmetric dithiocarbonate diester, an intermediate chlorothioformate is isolated and purified, and then reacted with a second mercaptan:

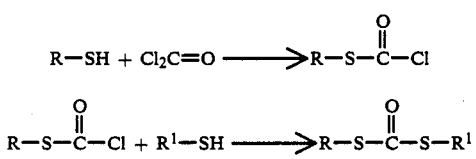

The use of a hazardous starting material such as phosgene is a serious disadvantage of the above described standard method of preparing dithiocarbonate diesters. Further, the synthesis of unsymmetrical dithiocarbonate diesters is not accomplished in a convenient and efficient manner.

Accordingly, it is an object of this invention to provide a process for preparing symmetrical and unsymmetrical dithiocarbonate diesters, without the use of a phosgene type of hazardous starting material.

It is another object of this invention to provide a process for dithiocarbonate diester production which proceeds via a novel isoxanthate salt reactant.

It is a further object of this invention to provide a novel class of isoxanthate salt compounds, and to provide a process for their production.

Other objects and advantages of the present invention shall become apparent from the accompanying description and examples.

DESCRIPTION OF THE INVENTION

One or more objects of the present invention are accomplished by the provision of a process for preparing isoxanthate salts which comprises reacting a metal mercaptide with carbonyl sulfide in a liquid medium under aprotic conditions.

In one embodiment, the present invention provides a process for preparing isoxanthate salts which comprises reacting a metal mercaptide with carbonyl sulfide in an aprotic solvent medium, wherein the metal mercaptide corresponds to the formula:

$$R-S-M$$

where R is an organic substituent selected from aliphatic and alicyclic groups, and M is a monovalent metal.

In another embodiment, the present invention provides a process for preparing isoxanthate salts which comprises reacting a metal mercaptide with carbonyl sulfide in an aprotic solvent medium, wherein the metal mercaptide corresponds to the formula:

$$R-S-M-X$$

where R is an organic substituent selected from aliphatic and alicyclic groups, M is a divalent metal, and X is a halogen atom.

The term "aprotic" as employed herein refers to a liquid reaction medium which is free of protons during the operation of a present invention process embodiment.

The present invention further provides a novel class of isoxanthate salt compositions corresponding to the formula:

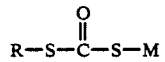

where R is an organic substituent selected from aliphatic and alicyclic groups, and M is an alkali metal.

In the R—S—M and R—S—M—X formulae disclosed above, R is a substituent selected from aliphatic and alicyclic groups. Illustrative of R substituents are methyl, ethyl, isopropyl, 2-butyl, decyl, dodecyl, methoxyethyl, methylthioethyl, chloroethyl, allyl, 2-hexenyl, benzyl, naphthylmethyl, cyclopentyl, cyclohexyl, 2-cyclohexenyl, cyclohexylmethyl, 4-chlorocyclohexyl, and the like. Preferably the R substituents contain between one and about twenty carbon atoms, and do not contain any functionality which interferes with the reaction between the metal mercaptide and the carbonyl sulfide.

In the metal mercaptide R—S—M formula, the metal M preferably is an alkali metal such as sodium, potassium and lithium.

In the metal mercaptide R—S—M—X formula, the metal M preferably is an alkaline earth metal such as magnesium, calcium and zinc, and the halogen X is chloride, bromide or iodide.

As illustrated in the Examples, the metal mercaptide can be prepared by reacting an appropriate mercaptan with a strong base such as alkali metal, alkali metal hydride, organometallic halide (e.g., Grignard Reagent), and the like, under aprotic and anhydrous conditions.

The product of a mercaptan reaction with alkali metal or alkali metal hydride is a R—S—M metal mercaptide. The product of a mercaptan reaction with Grignard Reagent is a R—S—M—X metal mercaptide.

The aprotic reaction medium is provided by solvents which have solubility properties which favor dissolution of mercaptans, metal mercaptans, carbonyl sulfide, alkali metal hydrides, Grignard Reagents, and the other components involved in the practice of the present invention process embodiments. Suitable aprotic media include polar solvents such as dimethylsulfoxide, methoxybenzene, 1,2-dimethylethane, 2-methoxyethyl ether, dioxane, tetrahydrofuran, dimethylformamide, and the like.

The term "polar" solvent refers to a solvent which is capable of at least partial water-miscibility, and which satisfies aprotic requirements for purposes of the present invention.

It is particularly preferred to maintain the aprotic reaction medium in a substantially anhydrous condition, since isoxanthate salt compositions are highly hygroscopic, and the presence of moisture tends to complicate the isolation and characterization of the product, or the further reaction of the product as described hereinafter.

In the above described process embodiments for the synthesis of the novel isoxanthate salt compositions, the metal mercaptide and carbonyl sulfide reactants can be employed over a wide range of molar ratios. Since carbonyl sulfide is a gas under standard conditions, it is convenient and efficient to introduce the carbonyl sulfide through a gas dispersion device into an aprotic liquid reaction medium containing the metal mercaptide. The addition of carbonyl sulfide is continued until the formation of isoxanthate salt product is completed.

The reaction between the carbonyl sulfide and metal mercaptide proceeds rapidly at a temperature between about $-20°$ C. and $50°$ C. The pressure in the reaction system can range from subatmospheric to superatmospheric, with ambient pressure being preferred. A typical reaction period will vary between about 0.1–1 hour.

The reaction between carbonyl sulfide and the metal mercaptide is exothermic, so that control of the reaction medium temperature usually requires the provision of cooling means.

PREPARATION OF DITHIOCARBONATE DIESTERS

The present invention further provides a process for producing a dithiocarbonate diester which comprises reacting an isoxanthate salt corresponding to the formula:

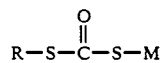

where R is a substituent selected from aliphatic and alicyclic groups, and M is an alkali metal, with a $R^1$—X organic halide in an aprotic solvent medium to yield a dithiocarbonate diester corresponding to the formula:

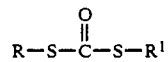

where R is a substituent selected from aliphatic and alicyclic groups, $R^1$ is a substituent selected from aliphatic and alicyclic groups, and X is halogen.

R and M in the formulae are as previously defined. The $R^1$ substituent can be aliphatic or alicyclic groups of the type previously described for R.

The halide substituent in the $R^1$—X halide reactant preferably is chloride, bromide or iodide.

The process can be conducted in an aprotic medium with approximately stoichiometric molar quantities of isoxanthate salt and $R^1$—X organic halide. The reaction proceeds efficiently at ambient pressure and a temperature between about $-20°$ C. and $50°$ C. in a sealed reactor system, over a period between about 0.5–20 hours.

In a further embodiment, the present invention provides a process for preparing a dithiocarbonate diester which comprises (1) reacting carbonyl sulfide with a R—S—M metal mercaptide in an aprotic solvent medium to form an isoxanthate salt intermediate corresponding to the formula:

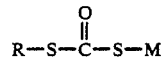

where R is a substituent selected from aliphatic and alicyclic groups, and M is an alkali metal; and (2) reacting the isoxanthate salt with a $R^1$—X organic halide in an aprotic solvent medium to produce a dithiocarbonate diester corresponding to the formula:

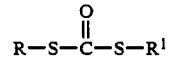

where R is a substituent selected from aliphatic and alicyclic groups, $R^1$ is a substituent selected from aliphatic and alicyclic groups, and X is halogen, as previously defined.

As an important advantage of the process embodiment, one reactor system can be employed to conduct the overall conversion of a metal mercaptide via an isoxanthate salt intermediate to the desired dithiocarbonate diester product.

An aprotic solvent medium is employed for the reaction of carbonyl sulfide with metal mercaptide to form an isoxanthate salt-containing solvent medium, and this serves as the reaction medium for the subsequent interaction of the isoxanthate salt with added alkyl halide to produce dithiocarbonate diester. The conditions of temperature and pressure for the conversion system can be as previously described.

The dithiocarbonate diester product can be recovered by conventional procedures, such as extraction, fractional distillation, and the like.

The following examples are further illustrative of the present invention. The catalysts and other specific ingredients and processing parameters are presented as being typical, and various modifications can be derived in view of the foregoing disclosure within the scope of the invention.

EXAMPLE I

This example illustrates the synthesis of sodium s-methylisoxanthate:

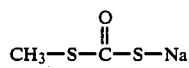

A 250 ml round-bottom flask was charged with 100 ml of dry tetrahydrofuran (THF, distilled from CaH$_2$ and stored over 4 Å molecular sieve) and 2.5 grams of finely divided sodium metal. The flask was cooled to 0° C. with an external ice bath and a two-fold excess of methyl mercaptan (CH$_3$SH, 10.4 grams) was added via syringe. A slow evolution of H$_2$ began immediately, accompanied by formation of a fine white powdery solid (CH$_3$SNa) suspended in the stirring THF medium. The reaction was allowed to continue at 0° C. for 24 hours, at the end of which time the suspension of white solid CH$_3$SNa was warmed to room temperature and stirred for 1.0 hour to allow the excess CH$_3$SH to evaporate (CH$_3$SH bp, 6.2° C.).

The suspension was then cooled to 0° C. and carbonyl sulfide (COS) gas introduced through a gas dispersion tube. The reaction commenced immediately. Gas was absorbed rapidly, and the temperature rose to 25° C. as all of the solid CH$_3$SNa dissolved in 5–10 minutes. COS addition was continued for 30 minutes, and the resulting pale yellow-green solution was stripped of solvent in vacuo to provide a viscous olive-green oil residue. After an extended period under vacuum, the oil solidified, and the resulting solid was broken up under dry ether. A fine powder was obtained by vigorous stirring, and the dark yellow ether was decanted. The solid was washed with two portions of dry ether and then dried under vacuum to yield 12.06 grams of pale green-white powder. The product was extremely hygroscopic, and samples exposed to the air began to dissolve in absorbed water and give off a strong odor of CH$_3$SH and COS within 15–30 seconds.

NMR and IR spectral data were consistent with the structure of sodium S-methylisoxanthate.

To confirm the structure of the product, it was converted to the stable dimethyl dithiocarbonate by reaction with methyl iodide. A sample of the powder (5.0 grams) was suspended in 75 ml of dry THF and a solution of 2.5 ml of CH$_3$I in 8.0 ml THF was added via syringe. The reaction mixture was allowed to stir at room temperature overnight and worked up by pouring into water. The aqueous material was extracted with diethyl ether, the combined ether extract washed with water, dilute aqueous Na$_2$S$_2$O$_3$, and water, and dried over MgSO$_4$. Removal of solvent in vacuo yielded 2.34 grams of pale yellow oil which was identified by NMR and IR as the expected product, dimethyl dithiocarbonate:

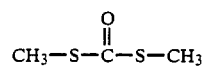

EXAMPLE II

This example illustrates the synthesis of sodium S-propyl isoxanthate:

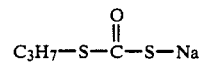

A 2.3 gram quantity of small sodium pieces was added to a stirred solution of 7.6 grams of 1-propanethiol/150 ml THF, and the mixture was reacted at room temperature for 24 hours. At the end of this period, the flask contained fine sodium 1-propanethiolate powder suspended in THF, which was then stirred as COS gas was bubbled in. The gas was absorbed with a mild exotherm, and dissolving of the suspended solid. After the reaction period, the solvent was removed in vacuo to provide a yellow solid, which was suspended and washed with ether. Vacuum-drying yielded 7.3 grams of sodium S-propylisoxanthate as an extremely hygroscopic off-white powder.

The identity of the solid was confirmed by isolation of the stable methyl derivative. A 5.0 gram sample was suspended in 150 ml dry THF, 4.54 grams CH$_3$I was added, and the mixture was stirred at room temperature overnight. The reaction mixture was worked up in the manner of Example I to yield 3.81 grams of pale yellow oil, which was identified by NMR and IR as methyl propyl dithiocarbonate:

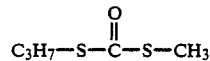

If cyclohexyl bromide is employed instead of methyl iodide, the product obtained is the corresponding cyclohexyl propyl dithiocarbonate:

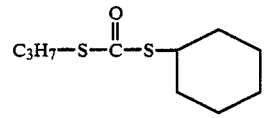

EXAMPLE III

This example illustrates the synthesis of sodium S-isopropylisoxanthate:

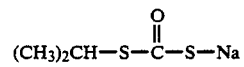

A suspension of 5.0 grams of 50% NaH/mineral oil in 150 ml dry THF was stirred, and 7.6 grams of 2-propanethiol added drop-wise. The mixture foamed vigorously as H$_2$ was evolved, and the grey suspension of NaH was replaced with a white suspension of sodium isopropylthiolate. The mixture was stirred until all H$_2$ evolution had ceased, and COS gas was then bubbled in until the solution ceased to absorb the added gas. Gas addition was continued for an additional 30 minutes, and the solvent was then removed in vacuo to provide a viscous dark-brown oil residue. Addition of dry ether with stirring caused sodium S-isopropylisoxanthate to precipitate as a fine powder. The precipitate was collected by vacuum filtration, washed with ether and vacuum-dried to 8.9 grams of brownish-white powder, which was the expected product. If KH is employed instead of NaH, the product obtained is potassium S-isopropylisoxanthate.

A 5.0 gram sample of the salt was added to 150 ml dry THF and stirred while 8.9 grams (two-fold excess) of $CH_3I$ was added in one portion. The mixture was stirred at room temperature overnight, and worked up in the usual manner to yield 2.97 grams of pale yellow-green oil, which was identified by NMR and IR as the methyl derivative, isopropyl methyl dithiocarbonate:

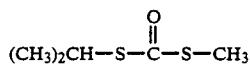

EXAMPLE IV

This example illustrates the preparation of sodium S-benzylisoxanthate:

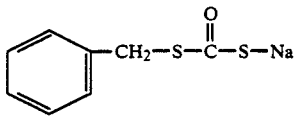

A 12.4 gram quantity of benzyl mercaptan was added dropwise to a suspension of 5.0 grams of 50% NaH/mineral oil in 150 ml dry THF, and the reaction mixture was stirred until $H_2$ evolution had ceased. The creamy white suspension of sodium benzylthiolate product was stirred at room temperature while COS was bubbled in until the solution no longer absorbed the gas, and then for an additional 30 minutes. The solvent was removed in vacuo to provide a viscous brown oil which, on addition of dry ether, precipitated a finely-divided white solid. The ether was decanted and the solid was washed with two portions of ether and pentane, then vacuum-dried to yield 18.32 grams of a free-flowing white powder of sodium S-benzylisoxanthate. The product was extremely hygroscopic, and exposure to air gave rapid solution in absorbed moisture and a strong odor of mercaptan.

The identity of the product was confirmed by reacting a 9.3 gram sample in 150 ml THF with 7.1 grams of $CH_3I$ at room temperature to yield 6.82 grams of yellow oil, identified as benzyl methyl dithiocarbonate:

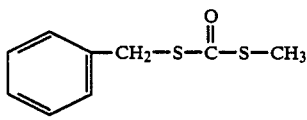

EXAMPLE V

This example illustrates the synthesis of bromomagnesium S-propylisoxanthate:

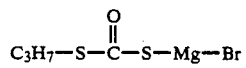

A solution of t-butylmagnesium bromide was prepared by reacting 2.43 grams of Mg shavings with 13.7 grams of t-butylbromide in 110 ml of dry THF. After the pale yellow-brown solution of Grignard reagent had cooled back to room temperature, a solution of 7.6 grams of 1-propanethiol in 50 ml of THF was added dropwise to generate the bromomagnesium thiolate in solution. The pale yellow-brown solution was stirred and COS gas bubbled in to generate a mild exotherm and a color change to pale yellow-green. After gas absorption had ceased, COS addition was continued for an additional 30 minutes, and the solvent was removed in vacuo to give an off-white residue which crystallized spontaneously. The solid was washed with dry ether and pentane, and vaccum-dried to yield 21.02 grams of white powder, which was identified by IR analysis as bromomagnesium S-propylisoxanthate.

Bromomagnesium S-isopropylisoxanthate was prepared by employing 2-propanethiol instead of 1-propanethiol. The product structure was confirmed by IR analysis.

EXAMPLE VI

This example illustrates the production of a dithiocarbonate diester in an aprotic reaction medium, via an in situ formed isoxanthate salt intermediate.

A variety of dithiocarbonate diesters was prepared in accordance with the following general procedure:

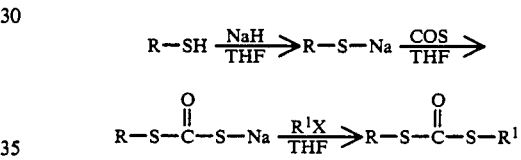

An equimolar amount of thiol was added to a suspension of NaH in THF (usually on a scale of 0.025 mols/100 ml THF) and the mixture stirred until all evidence of $H_2$ evolution had ceased. The resultant suspension of sodium thiolate was cooled to room temperature, and COS gas was introduced via a fritted glass gas dispersion tube. When evidence of gas absorption by the soluton had ceased, the gas addition was continued for an additional 15-30 minutes to ensure complete saturation. The resultant suspension of sodium isoxanthate was cooled to room temperature.

An equimolar amount of alkylating agent was then added in a single portion, in neat form if a liquid or as a solution in a minimum volume of THF if a solid. The flask then was sealed and stirred overnight at room temperature. Work-up was accomplished as previously described by pouring into water and extracting with either ether or chloroform. Drying of the organic extract over $MgSO_4$, vacuum filtration and removal of solvent in vacuo yielded the respective products, usually as pale yellow-green oils, which were identified on the basis of NMR and IR spectral analysis.

The dithiocarbonate diester products prepared are listed in the table.

TABLE

| R | $R^1$ | X | % Yield |
|---|---|---|---|
| $CH_3CH_2CH_2$ | $CH_3$ | I | 92.7 |
| $(CH_3)_2CH$ | $CH_3$ | I | 96.7 |
| $(CH_3)_3C$ | $CH_3$ | I | 72.6 |
| $\phi CH_2$ | $CH_3$ | I | 92.9 |
| $\phi CH_2$ | $CH_3CH_2CH_2$ | I | 96.1 |

TABLE-continued

| R | R¹ | X | % Yield |
|---|---|---|---|
| ØCH₂ | (CH₃)₂CH | I | 26.6 |
| ØCH₂ | p-Cl—Ø-CH₂ | Cl | 76.2 |
| ØCH₂ | CH₂=CH—CH₂ | Br | 98.9 |
| ØCH₂ | NC—CH₂ | Cl | 70.7 |

What is claimed is:

1. A process for preparing isoxanthate salts which comprises reacting a metal mercaptide with carbonyl sulfide in a liquid medium under aprotic conditions.

2. A process in accordance with claim 1 wherein the metal mercaptide corresponds to the formula:

R—S—M where R is an organic substituent selected from aliphatic and alicyclic groups, and M is a monovalent metal.

3. A process in accordance with claim 1 wherein the metal mercaptide corresponds to the formula:

R—S—M where R is an organic substituent selected from aliphatic and alicyclic groups, and M is an alkali metal.

4. A process in accordance with claim 1 wherein the metal mercaptide corresponds to the formula:

R—S—M—X where R is an organic substituent selected from aliphatic and alicyclic groups, M is a divalent metal, and X is a halogen atom.

5. A process in accordance with claim 1 wherein the reaction is conducted at a temperature between about −20° C. and 50° C.

6. A process in accordance with claim 1 wherein the aprotic liquid medium comprises a polar organic solvent.

7. A process in accordance with claim 1 wherein the isoxanthate salt product corresponds to the formula:

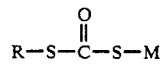

where R is an organic substituent selected from aliphatic and alicyclic groups, and M is an alkali metal.

8. Bromomagnesium S-propylisoxanthate.

9. Bromomagnesium S-isopropylisoxanthate.

10. A process for preparing a dithiocarbonate diester which comprises (1) reacting carbonyl sulfide with a R—S—M metal mercaptide in an aprotic solvent medium to form a isoxanthate salt intermediate corresponding to the formula:

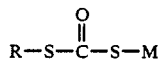

where R is a substituent selected from aliphatic and alicyclic groups, and M is an alkali metal; and (2) reacting the isoxanthate salt with a R¹—X organic halide in an aprotic solvent medium to produce a dithiocarbonate diester corresponding to the formula:

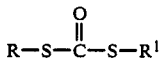

where R is a substituent selected from aliphatic and alicyclic groups, R¹ is a substituent selected from aliphatic and alicyclic groups, and X is halogen.

11. A process in accordance with claim 10 wherein the step(1) and step(2) reactions are conducted at a temperature between about −20° C. and 50° C.

12. A process in accordance with claim 10 wherein the aprotic solvent medium in the step(1) and step(2) reactions comprises a polar organic solvent.

13. A process in accordance with claim 10 wherein the step(2) reaction is conducted by adding the R¹—X organic halide to the aprotic solvent solution of isoxanthate salt intermediate produced in step(1).

14. A process in accordance with claim 10 wherein the R and R¹ substituents in the dithiocarbonate diester product formula are identical groups.

15. A process in accordance with claim 10 wherein the R and R¹ substituents in the dithiocarbonate diester product formula are different groups.

* * * * *